(12) United States Patent
Pison et al.

(10) Patent No.: US 9,750,952 B2
(45) Date of Patent: Sep. 5, 2017

(54) MAGNETIC INSTRUMENT FOR THE HOMING OF THERAPEUTIC CELLS AND THE ELIMINATION OF EXCESS THERAPEUTIC CELLS

(75) Inventors: Ulrich Pison, Berlin (DE); Wolfgang Meissner, Berlin (DE); Michael Giersig, Kleinmachnow (DE)

(73) Assignee: OGENO GMBH, Berlin (DE)

( * ) Notice: Subject to any disclaimer, the term of this patent is extended or adjusted under 35 U.S.C. 154(b) by 1035 days.

(21) Appl. No.: 13/878,991

(22) PCT Filed: Oct. 19, 2011

(86) PCT No.: PCT/EP2011/068276
§ 371 (c)(1),
(2), (4) Date: Jun. 21, 2013

(87) PCT Pub. No.: WO2012/052486
PCT Pub. Date: Apr. 26, 2012

(65) Prior Publication Data
US 2013/0261373 A1  Oct. 3, 2013

(30) Foreign Application Priority Data

Oct. 19, 2010 (DE) .................. 10 2010 049 052
Oct. 19, 2010 (DE) .................. 10 2010 049 072
Oct. 19, 2010 (EP) ....................... 10075714

(51) Int. Cl.
| | |
|---|---|
| *A61N 2/00* | (2006.01) |
| *A61N 2/02* | (2006.01) |
| *A61N 2/06* | (2006.01) |
| *A61B 10/02* | (2006.01) |
| *B03C 1/033* | (2006.01) |

(Continued)

(52) U.S. Cl.
CPC .............. *A61N 2/004* (2013.01); *A61B 10/02* (2013.01); *A61N 2/02* (2013.01); *A61N 2/06* (2013.01); *B03C 1/0332* (2013.01); *B03C 1/286* (2013.01); *G01N 33/54326* (2013.01); *A61B 10/0045* (2013.01); *A61B 10/0064* (2013.01); *A61B 10/04* (2013.01); *A61B 2010/0077* (2013.01);

(Continued)

(58) Field of Classification Search
CPC . A61B 10/0045; A61B 10/0064; A61B 10/02; A61B 10/04; A61B 2010/0077; A61B 2017/00876; A61N 2/06; A61N 2/004; A61N 2/02; B03C 1/286; B03C 2201/26; B03C 1/0332; G01N 33/54326
See application file for complete search history.

(56) References Cited

U.S. PATENT DOCUMENTS

| | | |
|---|---|---|
| 5,282,476 A | 2/1994 | Terwilliger |
| 5,782,764 A | 7/1998 | Werne |

(Continued)

FOREIGN PATENT DOCUMENTS

| | | |
|---|---|---|
| EP | 1779816 A2 | 5/2007 |
| WO | 9822022 A1 | 5/1998 |

(Continued)

*Primary Examiner* — Christine H Matthews
*Assistant Examiner* — Joshua D Lannu
(74) *Attorney, Agent, or Firm* — Agris & von Natzmer, LLP; Joyce von Natzmer

(57) ABSTRACT

The invention describes a system for the magnetic attraction of objects, which comprises a device with a magnetic element and at least one object having magnetic particles.

10 Claims, 9 Drawing Sheets

Figure 1:
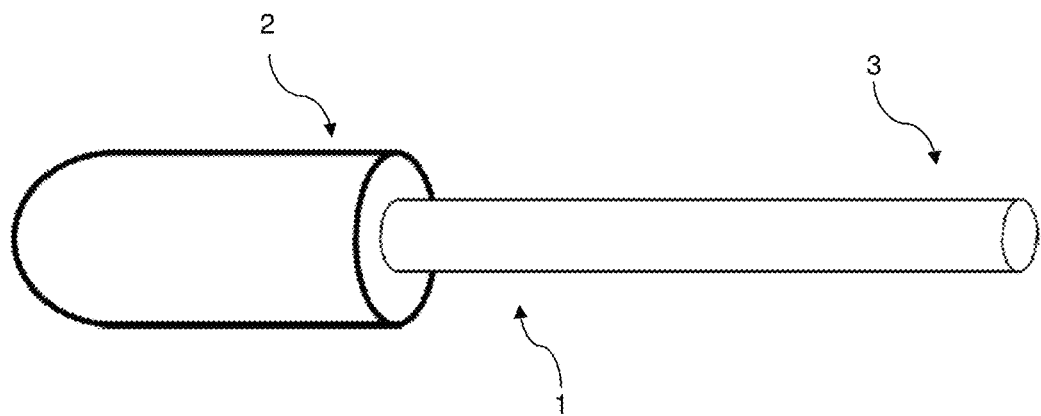

(51) Int. Cl.
   *B03C 1/28*      (2006.01)
   *G01N 33/543*    (2006.01)
   *A61B 10/00*     (2006.01)
   *A61B 10/04*     (2006.01)
   *A61B 17/00*     (2006.01)

(52) U.S. Cl.
   CPC . *A61B 2017/00876* (2013.01); *B03C 2201/26* (2013.01)

(56) References Cited

U.S. PATENT DOCUMENTS

| | | |
|---|---|---|
| 6,659,996 B1 | 12/2003 | Kaldany |
| 8,846,580 B2 | 9/2014 | Pison et al. |
| 9,247,928 B2 | 2/2016 | Pison et al. |
| 2002/0133225 A1* | 9/2002 | Gordon ............... A61F 2/82 623/1.42 |
| 2003/0135153 A1 | 7/2003 | Hagemeier |
| 2007/0173787 A1 | 7/2007 | Huang et al. |
| 2007/0231393 A1* | 10/2007 | Ritter ............... A61K 9/0009 424/489 |
| 2008/0312673 A1 | 12/2008 | Viswanathan et al. |
| 2010/0168609 A1 | 7/2010 | Pison et al. |
| 2011/0213270 A1 | 9/2011 | Pison |

FOREIGN PATENT DOCUMENTS

| | | |
|---|---|---|
| WO | 0123031 A1 | 4/2001 |
| WO | 2006131400 A1 | 12/2006 |
| WO | 2010/025719 A1 | 3/2010 |
| WO | 2010/078482 A1 | 7/2010 |
| WO | 2011047671 A1 | 4/2011 |

* cited by examiner

MAGNETIC INSTRUMENT FOR THE HOMING OF THERAPEUTIC CELLS AND THE ELIMINATION OF EXCESS THERAPEUTIC CELLS

This is the U.S. national stage of International application PCT/EP2011/068276, filed Oct. 19, 2011 designating the United States and claiming priority to European patent application 10075714.5, filed Oct. 19, 2010, German Patent application DE 10 2010 049 072.5, filed Oct. 19, 2010 and German Patent application DE 10 2010 049 052.0, filed Oct. 19, 2010.

The invention relates to a system comprising a magnetic device and at least one object having magnetic particles and also the use of this system for magnetic attraction of magnetically labeled therapeutic cells.

The homing of therapeutic cells (e.g., mesenchymal or embryonal stem cells) or of molecules in damaged tissue regions as part of regenerative medicine is not very satisfactory today. The methods that are currently used are limited to direct instillation (e.g., in infarct regions of the heart during a surgical procedure), arterial infusion or venous catheter based needle injection.

Therapeutic cells are often separated from other cells by immunomagnetic methods before being transplanted. Magnetic particles carrying antibodies directed against surface markers of therapeutic cells, e.g., CD 133 or CD 34, are used for this separation. Furthermore, it is customary to label the therapeutic cells with iron oxide nanoparticles to allow them to be located with the help of imaging methods after they have been transplanted into the body of the recipient.

The identification and separation of individual cell populations from blood in vitro is accomplished today using functionalized magnetic nanoparticles. The magnetic susceptibility of the particles plays an important role here because this behavior determines to a significant extent the magnetophoretic property of the particles used. The decoration of *E. coli* can be implemented successfully in vitro with magnetic nanoparticles, and magnetotactic bacteria can be imaged in vivo using imaging methods.

When material must be taken from a living human or animal body for microbiological diagnostic procedures, this is usually done by taking a solid tissue specimen through a biopsy or by taking bodily fluids, e.g., in the form of a vascular puncture, to obtain a blood sample or by pleural puncture to obtain a pleural effusion or by puncture of a joint to obtain synovial fluid or by a spinal tap to obtain cerebrospinal fluid or by puncture of a body cavity system in general to obtain material in liquid form or in a liquid-like form. Furthermore, smears of body regions are prepared for microbiological diagnostics. The state of the art has so far described biopsy instruments which use antigen-antibody interactions and ligand-receptor interactions in addition to the traditional punching, cutting and aspiration methods to obtain and/or enrich biopsy material.

In modern medicine, the biopsy, i.e., removal, of material from a living human or animal body for the purpose of testing by means of various methods, for example, microscopy is performed routinely. Such a method is typically used for diagnosis of malignant and premalignant cell transformations, which are indicative of the presence of cancerous or precancerous tumors. In the routine techniques, which are known as nuclear biopsies, entire tissue segments are taken for histological testing by making use of various types of hollow needle biopsy instruments. These instruments have cannulas with a sharp edge at the front or a notched stiletto for cutting into the tissue when introduced into the selected body area. The sample of tissue to be removed as a biopsy specimen is taken up into the cylindrical bore of the cannula. When the biopsy instrument is removed from the body, the specimen is kept in the cylindrical bore by mechanical means or by suction and is separated from the main body of the tissue in the extraction process. Specimens taken in this way typically have an elongated cylindrical shape in general or they have a longitudinal semicylindrical shape. The quality, e.g., the width, length and proportion of crushed cells of biopsy specimens for cytological or histological examination is an important factor, which influences the result of the test. Tissue biopsy specimens should reflect the structure of the living tissue as accurately as possible. Accordingly, stresses on the specimens in excision and separation from the tissue and in removal from the cannula should be avoided.

The state of the art has so far described biopsy instruments which use antigen-antibody interactions and ligand-receptor interactions to obtain the biopsy material in addition to using the traditional punching, cutting and aspiration methods.

U.S. Pat. No. 5,282,476 describes an automated instrument for performing a biopsy, in which the cannula is attached by a stiletto, which deflects the cannula to the biopsy site. After insertion, the cannula is driven beyond the stiletto, taking with it the specimen. Suction means are used to secure the specimen. However, this biopsy instrument has a relatively complex design because of the suction means and requires substantial skill in handling. In the hands of an untrained user, this instrument can give uncertain results. Furthermore, it is designed for removing material from solid body structures and not from body cavity systems.

In addition, there are known instruments or sensors which are used to enrich specimens. WO/2006/131400 describes the use of a functionalized surface for the enrichment and recovery of molecules or rare cells, e.g., fetal trophoblasts, from the maternal blood stream. To this end, receptor structures that are anchored on the surface of the sensor will react with specific cells or molecules in the blood stream and thus should permit an enrichment of this material in situ before it is removed from the body.

In addition, the state of the art contains descriptions of devices (for example, WO 01/23031 A1, EP 1 779 816 A2, US 2003/0135153, WO 98/22022 A1) with the help of which certain active ingredients or dyes can be introduced into body cavities. The active ingredients here are introduced into cavities in the device and are released on reaching the target position. One disadvantage here is that the specimens are delivered very inaccurately and the active ingredients are to be introduced into the device in liquid form. The possibilities for use of these devices are therefore greatly limited.

Furthermore, magnetic devices which are completely or essentially completely magnetic have been described in the state of the art. However, these devices do not permit optimal enrichment or withdrawal of specimens. In particular the known devices do not allow homing of magnetically labeled cells to be performed.

The means described in the state of the art for taking or enriching specimens cannot be used in all regions of the body. In particular, endoscopic use of instruments and/or sensors that have already been described is impossible or very difficult to perform. Other important disadvantages include the precision with which the tissue area selected for the biopsy, in particular the body cavity systems, can be located with the instrument/sensor, the simplicity with which the instrument and/or sensor can be handled, the injury done to the patient by the method as well as the cost of the instrument or sensor. Furthermore, there has not been any description of a biopsy instrument designed for use on humans and animals in order to permit an enrichment of the biopsy material at low risk prior to removal of the specimen from the body cavity system.

In applications of biopsy instruments, which seek to gain biopsy material by means of antigen-antibody interactions or by ligand-receptor interactions in general and are therefore implanted in the body for a defined period of time for enrichment purposes, it has been found that several factors make this enrichment difficult under flow conditions. These include the affinity of the ligand used for its corresponding receptor, the viscosity of the flow medium (e.g., blood in the circulation system), the flow conditions (flow rate, flow form), the size of the target object and the spatial distance over which the attractive forces should induce an attraction of analytes.

Against the background of this state of the art, the object of the present invention is to supply an instrument for magnetic attraction of objects that will not have the disadvantages or shortcomings of the state of the art.

This object is achieved by the independent claims. Preferred embodiments are derived from the dependent claims.

It was completely surprising that a system for magnetic attraction of objects could be made available, wherein the system comprises
  a. a device comprising the following components:
    i. a guide element comprising a spring-elastic distal area and a proximal area,
    ii. a magnetic function element, which is placed between the distal area and the proximal area of the guide element, and
    iii. a stabilizing element, which is connected to the proximal area of the guide element and
  b. at least one object having magnetic particles.

It was completely surprising that a system that would enable the magnetic attraction of objects could be made available. This system is preferably used to attract and bind magnetically labeled objects. In a preferred embodiment, the system is used for "homing" of therapeutic cells. "Homing" in the sense of the present invention refers in particular to bringing a certain type of cell "home" to its site of action. Those skilled in the art are aware that different cell types exist in a body but can be differentiated by means of various features. In the sense of the invention, a cell type refers to a cluster of cells which have a certain function within a body. Through their function, they often have a shape which corresponds to this function. Cells of the same cell type or of different cell types which are in close functional relationship form a tissue and various tissues which mutually support one another in their function, form an organ. Cell types include, for example, B-lymphocyte, blastomers, egg cells, red blood cells, fibroblasts, hepatocytes, myoblasts, nerve cells, osteoblasts, osteoclasts, sperm cells, stem cells, T-lymphocytes or zygotes. In the sense of this invention, this system may comprise in particular the device and/or one or more magnetically labeled objects, preferably paramagnetically and/or ferromagnetically labeled objects.

It was completely surprising that the homing of therapeutic cells could be improved with this system. Therapeutic cells are preferably (1) embryonal stem cells that can be obtained from blastocysts or they are (2) adult stem cells or (3) progenitor cells that can be derived from human tissue, preferably from the bone marrow, the umbilical cord or from blood components in general or (4) induced pluripotent stem cells (IPSCs), which are produced by genetic engineering methods or (5) embryonal cell lines or (6) autologous embryonal stem cells that can be obtained by therapeutic cloning. These therapeutic cell types (1) through (6) are preferably also referred to as objects and they have magnetic particles. To improve the homing of therapeutic cells in areas of damaged tissue, the magnetic particles, which are already being used either for cell separation or for cell labeling or are comparable, can also be used either for the cell separation or the cell labeling and are also used to bind the magnetic forces to a suitably designed magnetic instrument. This instrument is also referred to as an apparatus, in particular in the sense of the present invention. With the help of the magnetic instrument, therapeutic effects can preferably be brought close to damaged tissue areas via the blood vessel system or through direct tissue puncture in the vicinity of damaged tissue regions (homing).

Furthermore, it was surprising that a preferred system can be used to eliminate excess objects, in particular cells, from a body, so that the risk potential of therapeutic cells can be drastically reduced. This was completely surprising and has not yet been described in the state of the art. In a preferred embodiment the invention relates to the use of a system for magnetic attraction of therapeutic cells, wherein the system has
  a. a device comprising the following components:
    i. a guide element comprising a spring-elastic distal area and a proximal area,
    ii. a magnetic function element which is mounted between the distal area of the guide element and the proximal area and
    iii. a stabilizing element which is connected to the proximal area of the guide element and
  b. at least one therapeutic cell having magnetic particles.

Although some instruments designed specifically for cell transplantation are known in the state of the art, such as those disclosed by the company BioCardia Inc., the state of the art has not yet had any specially designed instruments which would improve or enable homing of therapeutic cells with the help of magnetic function elements. No instruments have been described yet for elimination of excess therapeutic cells. It has surprisingly been found that the use of magnetic function elements within an instrument results in a substantial improvement in the number of therapeutic cells in the damaged tissue regions, namely from max. 20% successful deposition at the present time to 60%.

A magnetic instrument for homing of therapeutic cells may have various designs. It may comprise a magnetic function element but it preferably comprises three elements, the guide element, the magnetic element and the stabilizing element. It is preferable for the functional element to be ferromagnetic or electromagnetic. The magnetic function element is arranged between the distal area and the proximal area of the guide element. A magnetic element or a magnetic function element in the sense of the present invention denotes in particular an element which advantageously has access to a magnetic field or can generate a magnetic field. The magnetic element may be made of a magnetic material or may comprise a magnetic alloy. However, it may also be preferable for a magnetic adhesive tape to be applied to the magnetic element.

Furthermore, it is preferable for the magnetic element to comprise magnetic materials, including metal, plastic and/or ceramic materials. In the sense of the present invention, these denote in particular materials which are magnetized under the influence of an external magnetic field, for example, in particular being permanently magnetized. The magnetic material advantageously comprise ferromagnetic materials in which the magnetization occurs due to possibly sudden alignment in the Weissian regions under the influence of an external magnetic field. Preferred ferromagnetic materials include iron in particular iron oxide or soft iron, silicon iron, permalloy, supermalloy, cobalt, nickel, Mn—Zn ferrites and Alnico V, lanthanoid gadolinium, terbium, dysprosium, holmium and erbium. Neodymium and/or samarium cobalt are preferred for use as the magnetic material. However, it may also be preferable to use an electromagnetic as the magnetic element. The electromagnet my advantageously be turned on and off. This makes it possible to activate the electromagnetic only when objects are to be attracted. An electromagnet includes in particular a coil which has a core of a ferromagnetic material. A magnetic attraction in the sense of the invention denotes the magnetic attraction of magnetic objects.

Compounds which do not have any ferromagnetic behavior, for example, chromium dioxide, manganese arsenide, europium(II) oxide, superfluid A-1 phase of He-3 or Heusler alloys may also be used advantageously as the magnetic element. However, paramagnetic including manganese, palladium and chromium or ferrites with the general composition $M(II)Fe(III)_2O_4$ or $M(II)O.Fe_2O_3$, which contain permanent magnet dipoles, may also be used advantageously as the magnetic element. Permanent magnets or hard magnets may preferably also be used as the magnetic element. Advantageous permanent magnets include AlNiCo—SmCo, $Nd_2Fe_{14}B$, $Ni_{80}Fe_{20}$ or NiFeCo alloys with the main constituents, for example, Cu, Ni, Al, Cu and Ti. Other preferred magnetic elements include PtCo, FeCoVCr and SECo alloys. Since the permanent magnets are very hard and brittle, magnetic function elements having surprising advantages can be shaped from them. For example, it has been found that an increase in surface area is achieved and more magnetic objects can be bound.

Metals in the sense of this invention preferably comprise aluminum, beryllium, bismuth, lead, chromium, iron, gold, indium, potassium, cobalt, copper, magnesium, manganese, molybdenum, sodium, nickel, osmium, palladium, platinum, rhodium, ruthenium, silver, tantalum, titanium, vanadium, tungsten, zinc, tin or zirconium. Ceramic materials are an umbrella concept for materials composed of inorganic and primarily nonmetallic compounds or elements and more than 30 vol % crystallized materials. Ceramic materials include alumina or kaolin, quartz, feldspar, limestone, silimanite, magnesite, terra cotta, majolica, faience, raku, paper clay or oxide ceramics. For the advantageous embodiment, plastics may also be used. The advantageous embodiment ensures that an effective and rapid magnetic attraction of magnetic objects by the magnetic element is achieved and the collected material is bound to the magnetic element and remains there. An increase in the surface area of the materials is also possible to additionally increase the efficacy of the attraction. It has been found that effective magnetic binding of magnetic objects in vessels where a high flow prevails, for example, is possible with this magnetic element. This was completely surprising and constitutes a substantial advantage in comparison with the state of the art. Due to the preferred magnetic properties of the magnetic element, objects, in particular magnetically labeled therapeutic cells, can be enriched, i.e., objects that are not in the near environment of the instrument, i.e., the device, because the magnetic forces act over a greater distance than antigen-antibody binding forces, for example. However, the magnetic forces created by the magnetic element surprisingly have no negative effect on tissues or organs because these forces are weaker than those with the magnetic biopsy devices described in the state of the art.

The magnetic element may preferably have on its surface detection molecules which are applied to its surface by means of chemical, electrochemical and/or biological methods. It is also preferable for the distal area of the spring-elastic guide element to have detection molecules. Detection molecules are also known to those skilled in the art as scavenger molecules. These are molecules which preferably interact with organic and inorganic materials. Organic materials include polymers, for example. Approximately 90% of the organic materials are formed from carbon, hydrogen and oxygen in varying quantity ratios. However, organic compounds may also contain nitrogen, sulfur, phosphorus and halogens but also other elements or combinations of these. In addition, metal organic materials including those having a compound of metal and/or carbon may be used. Inorganic materials, i.e., those not consisting essentially of carbon, may be materials comprising types of glass, ceramic, hard substances, nanostructured and nanocrystalline silicon or silicates. Thus, due to the special design of the magnetic element, homing or extraction and/or elimination of special cells or molecules may take place in situ, i.e., within the body of human or animal, which thus represents a reversal from what is customary in the state of the art and solves a long-standing problem. This specificity is achieved by the fact that only magnetically labeled cells or objects are attracted and bound by the magnetic function element. A rapid effect can be achieved in this way, so that the burden on the patient is relieved and the patient is protected. Extraction or elimination in the sense of the invention denotes in particular the removal of magnetically labeled objects from a body.

In another advantageous embodiment, it is provided that the detection models are preferably selected from the group comprising antibodies, antibody fragments, synthetic protein scaffolds, peptides, nucleic acids, receptors and/or inorganic materials. The application of detection molecules to the magnetic element achieves an increased specific enrichment of labeled cell types in situ. The detection molecules may react with cells and/or molecules in the body of human or animal and bind the cells and/or molecules. Various detection molecules may be used for this purpose and may also be combined with one another. Due to the specific positioning of the instrument in a desired body region and due to the specificity and sensitivity of the instrument, it is possible to achieve the result that the homing or the extraction of magnetically labeled cells takes place much more rapidly and also lower concentrations of molecules and/or cells are detected by the detection molecules. This constitutes a technical advance. In addition, a wide field of applications of advantageous embodiments is conceivable by varying the detection molecules. It may also be advantageous to apply different detection molecules to the magnetic element. Thus, different detection molecules which are specific for a single cell type or for a certain cell type, for example, may be applied. This ensures that preferably one specific cell type is attracted. The molecules or cells are attracted rapidly and efficiently and thus reach the site of action much more rapidly. Furthermore, specific cell types can be collected more quickly in this way.

In the proximal area of the guide element, the stabilizing element is located and is fixedly bound to this area or may be designed to be freely displaceable. The components of the instrument are preferably arranged sequentially from distally to proximally. The magnetic element is arranged after the distal spring elastic guide element, such that the stabilizing element is situated in the proximal area of the guide element. The magnetic element is advantageously secured by the proximally located stabilizing element. This prevents dislocation of the components and loss of a component. Furthermore, reliability is increased by the sequential arrangement of components and the efficiency of magnetic attraction is improved. It is possible for a knowledgeable person skilled in the art to construct special forms of the instrument in which a magnetic element with different detection molecules is arranged between the distal and proximal portions of the guide element or the functionalization of the distal part of the guide element with detection molecules takes place while preserving the spring elastic material properties of this region.

It is also preferable for the distal region of the device, i.e., the spring elastic portion of the guide element to be made of nonmagnetic metallic or nonmetallic materials. Accordingly, in a preferred embodiment, it may also be made of stainless steel or other metals. Metals are chemical elements which, in contrast with the nonmetals, are located at the left of the diagonal dividing line in the periodic system, starting with the element beryllium (group 2) to polonium (group 16) as well as their alloys and intermetallic compounds (comprising Laves phases, Heusler phases, Zintl phases, Hume-Rothery phases, NiTi, $Co_s$, $Nb_3Sn$ or $Ni_3Al$) with characteristic metallic properties. Metals include aluminum, beryllium, bismuth, lead, chromium, iron, gold, indium, potassium, cobalt, copper, magnesium, manganese, molybdenum, sodium, nickel, osmium, palladium, platinum, rhodium, ruthenium silver, tantalum, titanium, vanadium, tungsten, zinc, tin or zirconium. In one advantageous embodiment, an internal wire may be surrounded by an outer wire in the circular arrangement, so that the spring elastic property is achieved. It should be emphasized that only the magnetic element consists of a magnetic material in the sense of this invention.

In another embodiment, the instrument in particular the distal region of the guide element may be made of nonmetallic materials from which thin cylindrical structures can be formed. Preferred nonmetals include boron, carbon, phosphorus, sulfur, iodine or astatine. A cylinder in the sense of this invention is in particular an area bordered by two parallel planar surfaces (base area and cover area) and a jacket or cylindrical area formed by parallel lines. However, it may also be preferable for the distal area to have an angular shape.

For nonmetallic materials, polymer may be used in a preferred embodiment. Polymers in the sense of this invention denote in particular a substance composed of a collection of macromolecules (polymer molecules) which have a uniform chemical composition but are usually different with regard to the degree of polymerization, the molecular weight and the chain length. Such uniform polymer substances are all macromolecules, preferably having the same structure, and differing only in their chain length (degree of polymerization). Such polymers can be referred to as polymer homologs. Polymers may be selected from the group comprising inorganic polymers, metal organic polymers, fully or partially aromatic polymers, homopolymers, copolymers, biopolymers, chemically modified polymers and/or synthetic polymers and they include polyethylene, polypropylene, polyvinyl chloride, polystyrene, polymethyl methacrylate, polyamide, polyester, polycarbonate, polyethylene terephthalate, polyethylene glycol, dendrimers, silicones, proteins, DNA, RNA, carbohydrates or polyhydroxyalkanoates. Polytetrafluoroethylene is preferred. The distal region of the device made of these materials constitutes a technical advance because the risk of injury is reduced by this preferred embodiment. The material has spring-elastic properties and thus prevents injury or damage to surfaces with which the device comes in contact.

It is also advantageous that the stabilizing element of the instrument has essentially a cylindrical design. Due to the advantageous embodiment, the stabilizing element can easily be applied to the proximal region of the guide element by pushing it on to the proximal region. In addition due to the advantageous cylindrical shape, easy insertion and extraction of the instrument can be achieved and thus the efficacy can be increased.

It is also advantageous that the stabilizing element can be pushed over the proximal portion of the guide element. The stabilizing element can be applied over the proximal region of the guide element without having to remove the additional components, essentially the magnetic element. The stabilizing element secures the magnetic element, which is accomplished by manufacturing the component with an accurate fit. An accurate fit in the sense of the invention denotes in particular that at least two components are manufactured so that they are compatible and fit accurately in the position intended for them. The ease with which the stabilizing element is applied to the proximal region of the guide element facilitates the work of those skilled in the art.

In another preferred embodiment it is provided that the outside diameter of the stabilizing element is preferably equal to the outside diameter of the distal region of the guide element. In this way a planar, i.e., flat surface of the element is formed so that injury to the patient is greatly reduced. Furthermore, it has been found that the efficiency of the homing process can be improved because the instrument can be introduced more easily and more flexibly into body cavities and is easier to maneuver.

Another advantageous embodiment of the system comprises an instrument, wherein the stabilizing element is reversibly connected to the proximal region of the guide element. According to this embodiment, the stabilizing element can preferably be removed again from the proximal region of the guide element to release the magnetic element. The magnetic element can be sent to the appropriate processing locations to perform subsequent diagnostic procedures or an analysis of the enriched magnetic objects in particular therapeutic cells may be performed on site. The advantageous embodiment constitutes a technical advance because those skilled in the art can assemble the instrument easily and can then also break it down again into the individual components. The stabilizing element may thus be reused repeatedly after appropriate disinfection, thereby reducing costs.

It is also advantageous if the stabilizing element is preferably made of plastic. Plastics are materials whose essential components consist of those macromolecular organic compounds which are formed synthetically or by modification of natural products. They are meltable and shapeable under certain conditions (heat and pressure) in many cases. Plastics also include rubbers and chemical fibers. The synthetic paint raw materials and adhesives may be included with the plastics. For the advantageous embodiment, plastics from the group of modified natural substances, synthetic plastics (polycondensates, polymers, polyadducts), thermoset plastics and/or unsaturated polyester resins comprising cellulose nitrate, cellulose acetate, cellulose esters, cellulose ethers, polyamide, polycarbonate, polyester, polyphenylene oxide, polysulfone, polyvinyl acetal, polyethylene, polypropylene, poly-1-butene, poly-4-methyl-1-pentene, ionomers, polyvinyl chloride, polyvinylidene chloride, polymethyl methacrylate, polyacrylonitrile, polystyrene, polyacetal, fluorine plastics, polyvinyl alcohol, polyvinyl acetate, poly-p-xylylene, linear polyurethanes, chlorinated polyethers, casein plastics, phenolic resin, urea resin, thiourea resin, melamine resin, epoxy resin, crosslinked polyurethanes, alkyd resin, allyl resin, silicone, polyimide and/or polybenzimidazole may be used. Through the use of plastic in the embodiment of the stabilizing element, instruments with rubber elastic properties can be produced which can be placed in different locations in the body. Due to the advantageous embodiment, an increased reliability and flexibility in performing homing or extraction of cells can be achieved. The risk of injury to the patient is also drastically reduced because the rubber elastic embodiment does not injure or damage surfaces. In addition, costs are reduced due to the use of plastics for the design.

It is also preferable for the stabilizing element and the proximal region of the guide element to be mechanically connected, glued and/or welded. This achieves a stable connection of the proximal region of the guide element and of the stabilizing element so that handling of the instrument is facilitated for those skilled in the art. Through a mechanical connection, the connection can be designed to be reversible, for which purpose fastening means known to those skilled in the art may be used. In addition, bonded or welded joints which are also familiar to those skilled in the art permit a secure and permanent connection of the proximal region and of the stabilizing elements.

In addition, it is advantageous that the guide element and the stabilizing element are manufactured in a manufacturing process, i.e., materials which are coordinated with the corresponding body regions in terms of both size and shape may be used for both components for one application. An advantageous embodiment comprises a plastic from the group of modified natural substances, synthetic plastics (polycondensates, polymers, polyadducts), thermoset plastics and/or unsaturated polyester resins, comprising cellulose nitrate, cellulose acetate, cellulose mixed esters, cellulose ethers, polyamide, polycarbonate, polyester, polyphenylene oxide, polysulfone, polyvinyl acetal, polyethylene, polypropylene, poly-1-butene, poly-4-methyl-1-pentene, ionomers, polyvinyl chloride, polyvinylidene chloride, polymethyl methacrylate, polyacrylonitrile, polystyrene, polyacetal, fluorine plastics, polyvinyl alcohol, polyvinyl acetate, poly-p-xylylene, linear polyurethanes, chlorinated polyethers, casein plastics, phenolic resin, urea resin, thiourea resin, melamine resin, epoxy resin, crosslinked polyurethanes, alkyd resin, allyl resin, silicone, polyimide and/or polybenzimidazole. It is possible in this way to reduce the risk of injury for the patient because a planar surface of the instrument is obtained. The handling of the device is also simplified for those skilled in the art and the production costs for them can be kept low.

In an advantageous embodiment, it is provided that the magnetic element has an essentially cylindrical shape, but other geometric shapes may also be used including the polygon, triangle, rectangle, pentagon, hexagon, heptagon, octagon, nonagon, decagon, ellipse, circle, hyperbola, parabola, superellipse, spherical triangle, cycloids, rosette, helix, sphere, ellipsoid, rotational ellipsoid, paraboloid, rotational paraboloid, hyperboloid, oloid or polyhedron and/or combinations of these or other shapes. For this embodiment the magnetic element can easily be applied to the guide element from proximally, such that after application it is secured spatially by the spring elastic distal area and the proximal stabilizing element. This prevents dislocation of the magnetic element. Furthermore, it has been found that more efficient homing of magnetically labeled therapeutic cells is achieved due to the preferred shape because the magnetic field strength of the magnetic element is increased. Furthermore, the surface area can be increased in this way, so that again a higher number of magnetically labeled therapeutic cells can be removed from the body.

The magnetic element advantageously has an outside diameter which is larger than, equal to or smaller than the outside diameter of the distal area of the guide element, preferably 0.01 to 0.1 mm smaller. The advantageous embodiment achieves the result that the magnetic element can be applied to the guide element from proximally but is spatially limited by the distal area. The outside diameter of the magnetic element is 0.0001 to 5 mm, preferably 0.001 to 1 mm, especially preferably 0.01 to 0.1 mm smaller than the outside diameter of the distal region of the guide element. An almost planar surface of the device can be created due to the preferred outside diameter of the magnetic element, which is surprisingly ensures optimal functionality of the device because there is no interaction with biological surfaces during the insertion and removal of the device and therefore the positioning of the device is not impaired. It has also been found that an especially efficient magnetic attraction of magnetically labeled cells can be achieved through the preferred outside diameter, and the device can be sterilized and cleaned more rapidly and more easily. The outside diameter of the device or the instrument and accordingly the outside diameter of the magnetic element are preferably based on the anatomical structure into which the instrument is to be inserted. The length depends on the puncture site and the positioning for collection of the specimen in situ. The dimensions of the instrument can be adjusted easily and quickly to the requirements of the different sites of application, which results in time savings and cost reductions. It is preferable for the system to be inserted into a body by way of a vascular assess in particular.

In addition, it is advantageously provided that the guide element has a receiving device between the distal and proximal areas, such that the receiving device may involve recesses in various geometric shapes, comprising polygon, triangle, rectangle, pentagon, hexagon, heptagon, octagon, nonagon, decagon, ellipse, circle, hyperbola, parabola, superellipse, spherical triangle, cycloids, rosette, helix, sphere, ellipsoid, rotational ellipsoid, paraboloid, rotational paraboloid, hyperboloid, oloid or polyhedron and/or combinations of these or other shapes. One advantageous embodiment comprises cylindrical, semicylindrical, clasp-shaped or film-shaped recesses. These are examples which should not constitute a restriction on the receiving device. Film-shaped in the sense of this invention denotes in particular the fact that the receiving device or the magnetic element is shaped so that it has a very small thickness and a very large area. The magnetic element is preferably shaped according to the shape of the receiving device. These design alternatives ensure that a stabilizing element is connected following a magnetic element due to the advantageous arrangement of a distally located guide element. The advantageous embodiment can be adapted easily to different homing methods or cell extraction methods such that the quantity of cells to be bound can be varied and adapted to the needs of the user through the shape of the receiving device and/or of the magnetic element.

It is advantageously provided that the instrument additionally has a cover device. The cover device preferably has a sleeve-shaped structure which covers the magnetic element. Other geometric shapes including the polygon, triangle, rectangle, pentagon, hexagon, heptagon, octagon, nonagon, decagon, ellipse, circle, hyperbola, parabola, superellipse, spherical triangle, cycloids, rosette, helix, sphere, ellipsoid, rotational ellipsoid, paraboloid, rotational paraboloid, hyperboloid, oloid or polyhedron can also be used. Therefore the magnetic element and the cells bound there can be protected from shearing or deformation before being removed from the body and contamination outside of the body can be prevented. According to an advantageous embodiment, the cover device is a sliding device which is shifted from the proximal area over the magnetic element. However, other devices including folding devices which serve to cover the magnetic element are also conceivable. Due to the advantageous embodiment, the extracted cells are protected so that measurement errors are reduced and the quality of the extraction is improved. Furthermore, it has surprisingly been found that the homing of magnetically labeled therapeutic cells is improved by the cover device because the cover is preferably placed over the magnetic element and thus the magnetic effect of same can be used in a targeted manner. For example, the cover may be removed at the site of action so that the magnetic effect of the element is not manifested until it reaches the site of action.

It is advantageous that the cover device preferably covers the magnetic element such that the cover device comprises in particular homopolymers, copolymers, biopolymers, chemically modified polymers and/or synthetic polymers. Suitable materials for the cover device include polymer materials comprising polyethylene, polypropylene, polyvinyl chloride, polystyrene, polymethyl methacrylate, polyamide, polyester, polycarbonate, polyethylene terephthalate, polyethylene glycol, dendrimers, silicones, proteins, DNA, RNA, carbohydrates or polyhydroxyalkanoates, preferably polytetrafluoroethylene. In particular when the adjacent components are made of the same material, this yields a good displaceability of the individual components. Due to the advantageous embodiment, the cover device can easily be shifted over the magnetic element or may cover it. Due to the advantageous embodiment, errors in extraction of magnetically labeled cells are reduced and thus the efficiency is improved and the labor involved is reduced. It should be pointed out that the system according to the invention is used only for homing and extraction of magnetically labeled therapeutic cells and is not used for performing a biopsy, i.e., for removing specimen material. It was completely surprising that the system comprising a magnetic function element could be used for homing of magnetically labeled therapeutic cells and optionally for the extraction of excess magnetically labeled therapeutic cells. Nothing of this type is described in the state of the art. It was completely surprising for the inventors that therapeutic cells could be brought to their site of action more quickly by using the magnetic function element. Furthermore, unused cells can be removed easily and quickly in this way.

According to another advantageous embodiment, the instrument has a longitudinal borehole to receive preferably a mandrel and/or other function elements. The borehole may be created in the instrument by methods with which those skilled in the art are familiar, and the width of the borehole depends on the application and may be buried accordingly. For example, a mandrel (a guide wire) can be inserted into the longitudinal thin bore channel and advanced into the distal end of the instrument. This makes it possible to optimize the rigidity of the instrument for placement maneuvers in the body. Furthermore, additional functionalizations, e.g., of an electronic type, can also be introduced into such a borehole to increase the usability of the instrument. The longitudinal borehole improves the reliability in use and constitutes a simplification.

In a preferred embodiment, magnetic particles lie on the surface of the objects or are present inside the objects; in particular the particles lie on the surface of or inside of the object. The magnetic particles preferably have at least three magnetic individual domains in a biodegradable matrix, such that the magnetic property of the particles is preferably of a paramagnetic nature. Such magnetic particles may be made of alkali metals, alkaline earth metals, rare earth metals or transition metals or alloys thereof and they have a diameter of 3 nm to 3 µm, preferably 10 m to 200 nm. Alkali metals preferably include lithium, sodium, potassium, rubidium, cesium and francium. Alkaline earth metals preferably include beryllium, magnesium, calcium, strontium and barium. Rare earth metals include in particular the elements of group 3 of the periodic system and the lanthanoids. These are preferably the elements scandium, yttrium, lanthanum, cerium, praseodymium, neodymium, promethium, samarium, europium, gadolinium, terbium, dysprosium, holmium, erbium, thulium, ytterbium and lutetium. It was completely surprising that the preferred metals may be used to label the cells or objects so that they are attracted magnetically by the device. The magnetic field of the elements is surprisingly designed so that the function of the cells is not impaired. Furthermore, the paramagnetic elements are preferred because paramagnets are magnetic only as long as they are in the vicinity of a magnetic. They are magnetized in an external magnetic field such that the magnetic field is enhanced in its interior but exists only as long as the external magnetic field. Paramagnetic particles have the special property of being drawn into the magnetic field of the magnetic element. It was completely surprising that the device in combination with the magnetic particles and/or the magnetically labeled objects, in particular cells, would enable homing and extraction of cells. The present invention may thus be regarded as a combination invention because it is only through the combination of the known elements—magnetic device and/or instrument and magnetic particles—that synergistic effects occur, permitting efficient homing and specific extraction of excess cells. This effect exists in particular in that the paramagnetic properties of the particles occur only through the inclusion of the magnetic element of the device and this does not constitute any risk to tissues or organs. This was completely surprising and permits accurate control or guidance of the therapeutic cells having magnetic particles to a site of action. Nothing of this type is described in the state of the art and also permits inexpensive production of the system. Furthermore, it has been found that the cells, in particular therapeutic cells can be labeled more easily with paramagnetic particles because the interaction between the particles is negligible. In this way the particles can be made available by a mass production method. Due to this special design of the magnetic element of the device, a uniform magnetic field is generated, which is optimally adapted to the structures of body cavities, for example, and uniformly attracts the magnetically labeled cells, in particular therapeutic cells and thus ensures an optical distribution of the cells at the site of action.

Therapeutic cells are often separated from other cells by immunomagnetic methods before being transplanted. For this separation magnetic particles which carry the antibodies directed against surface markers of therapeutic cells are used (e.g., CD 133 or CD 34). Furthermore, it is customary to label the therapeutic cells with magnetic particles such as iron oxide nanoparticles to facilitate retrieval of them with the help of imaging methods after they have been transplanted into the body of the recipient. The labeling of the therapeutic cells is done routinely by incubated the objects with suitable magnetic particles for a period of preferably 10 minutes to 24 hours, preferably for 1 to 4 hours. To do so, the magnetic particles must be in a colloidally stable form, so that they either adhere to the objects from the outside or are absorbed by them and are then present in the cell interiors. The uptake of the magnetic particles may be improved preferably by transfection means (i.e., nonionic surfactants, lipids or polymer/nucleic acid complexes), by energy (electroporation), by a change in the osmolarity gradient (use of hypertonic/hypotonic buffer systems) or by other aids (e.g., scaffolds comprising electrically conductive nanotubes) or a mixture of these methods. It was completely surprising that the objects, preferably cells, especially preferably therapeutic cells could be labeled with magnetic particles such that they have at least three individual magnetic domains and are present in a biodegradable matrix with a total diameter of 10 mm to 3 µm. The particles are preferably colloidally stable in aqueous solutions, such that the biodegradable matrix is in particular a synthetic polymer or copolymer, a starch or a derivative thereof, a dextran or a derivative thereof, a cyclodextran or derivative thereof, a fatty acid, a polysaccharide, a lecithin or a mono-, di- or triglyceride or a derivative therefore or mixtures thereof. It is preferable that the magnetic particles may also contain a rare earth metal ion in addition to magnetite, iron oxide or maghemite or mixture thereof. These particles preferably have a spherical shape but other shapes may also be preferred. However, it has been found that spherical particles are more stable in their interaction with cells and also penetrate the cells so that a long lasting magnetic labeling of the cells is achieved. However, it may also be preferable for the particles to bind to antibodies, which in turn have a specific interaction with the cells to be labeled and thus the particles are located only at the surface of the cells. It has been found to be advantageous if the magnetic particles contain iron oxide in a percentage amount by weight of 0.1% to 60%, preferably 5% to 50%, especially preferably 15% to 40%. In this way an especially strong magnetic labeling of the cells may be achieved so that a rapid and in particular specific homing of these cells is achieved. This means that the cells labeled in this way, preferably therapeutic cells, can be brought rapidly and specifically to their site of action by the instrument. Furthermore, a rapid and specific extraction of the excess cells is also possible.

The present invention also relates to an attraction kit for magnetic attraction of objects comprising a device and at least one object having magnetic particles such that the device, which can also be referred to as an instrument in the sense of the present invention, comprises the following components:
  i. a guide element comprising a spring elastic distal area and a proximal area,
  ii. one or more magnetic elements which are attached between the distal area and the proximal area of the guide element and
  iii. the stabilizing element which is connected to the proximal area of the guide element,
wherein the guide element, the magnetic element and the stabilizing element are arranged sequentially from distally to proximally.

The kit comprises at least one guide element, a magnetic element and a stabilizing element such that the guide element, the magnetic element and the stabilizing element are arranged sequentially from distally to proximally. The guide element has a distal area and a proximal area, and the distal area is designed to have spring elasticity. It may also be advantageous to design special forms of the instrument in which the magnetic element comprises two or more magnetic partial elements with different detection molecules and is arranged between the distal portion and the proximal portion of the guide element. It may also be preferable to supply at least one magnetic element without detection molecules. The functionalization of the distal portion of the guide element may advantageously be accomplished using detection molecules and the spring elastic material properties of this region are preserved.

At least one magnetic element is mounted between the distal area and the proximal area of the guide element, serving in particular to magnetically bind magnetic nanoparticles, magnetized cells or objects. Thus due to the special design of the magnetic element, an accumulation of special cells in the body of a person or animal, i.e., in situ may occur, which constitutes a departure from that which is the usual technically and solves a long-term problem of the state of the art. Rapid extraction of magnetically labeled cells is achieved due to the high specificity of the magnetic element, while protecting the patient and relieving the burden on the patient. Furthermore, the extraction may take place in a system characterized by a high flow.

The kit is preferably used for homing of magnetically labeled therapeutic cells and their extraction. It was completely surprising that a kit could be make available that would make it possible for those skilled in the art to magnetically label objects, preferably cells and guide them to a site of action in a body with the help of the instrument. The kit is easy to operate by those skilled in the art and reduces the risk of injury for the patient. Additional advantages include the low cost of the kit and a high flexibility in design for different sites of use and application cases even utilizing additional aids, e.g., endoscopes.

The kit which is made available makes it possible to position the components needed for extraction of magnetically labeled cells and to keep them in the body for the required period of time. Visual or other guidance labels on the components of the kit are used for proper positioning; these labels may be made by engraving, color or tactile or signaling labels and may permit geographic positioning of the instrument during its positioning inside the body and for the process of removal of the instrument from the body. The positioning of the instrument can be ensured by means of imaging methods in situ. To do so, those skilled in the art can use known contrasting agents in the creation of the kit. The kit may also be adapted to special sites of use with regard to the dimensioning of the individual components and may be supplemented by aids to make available the necessary or desired components for special applications. In addition, the kit may be supplied as a disposable article, which better fulfills the hygienic demands of medical facilities.

The kit may advantageously be used for taking specimens, preferably from the blood vessel system, including the chambers of the heart, the pulmonary circulation and the blood circulation as well as the arterial and venous system as special biopsy locations, the gastrointestinal tract where the instrument may optionally be positioned either orally or anally, from the efferent glandular ducts of the pancreatic glands, lacrimal glands, parotid glands and the efferent glandular ducts of the mucous glands, of mixed glands of the skin and appendages, including the mammary glands, the spinal cord or the cerebral ventricular system, the gallbladder and its efferent anatomical structures, the efferent urinary tract or the lymphatic system or for taking specimens from body cavities of the abdomen or the chest, the uterus, the urogenital system or an intra-articular space.

The system or the kit is preferably used for magnetic attraction of therapeutic cells, preferably in the blood vessel system, in the efferent glandular ducts of the pancreatic gland, lacrimal gland, parotid gland, efferent glandular duct of the mucous glands, mixed glands, skin and appendage glands, mammary gland, spinal cord, cerebral ventricle system, peridural space, gallbladder and its efferent anatomical structures, efferent urinary tract or the lymphatic system, body cavities of the abdomen, the chest, the uterus, the urogenital system or a joint or the gastrointestinal tract. A preferred area of use is the body's blood vessel system. In this case the kit or the instrument is positioned above an indwelling cannula in the vascular system. Although the outside diameter of instrument is based on the diameter of the blood vessel for use in the vascular system, the length depends on the puncture site and the position for homing and extraction of magnetically labeled cells in situ. The outside diameter in placement in the pancreatic duct, in the choledochus duct, in the cystic duct or in the efferent urinary tract or the urinary bladder or the peritoneum or the tracheobronchial tree or the pleural cavity or an intra-articular space may be adjusted accordingly. The advantageous embodiments and dimensions can thus be determined quickly and easily by adaptations by those skilled in the art. Thus this solves a problem that has been existence in the state of the art for a long time and it makes available a fast and specific embodiment which can be used preferably in body cavity systems in different areas of the body and does not have the disadvantages of the state of the art.

The use of a kit is advantageous if the instrument is positioned by using endoscopic aids, preferably a gastroduodenoscope, cystoscope, urteroscope, rectoscope, proctoscope, coloscope, arthroscope, laparoscope, colposcope, hysteroscope, ophthalmoscope, laryngoscope and/or bronchoscope. In the sense of the present invention, an endoscope is a device with which the interior of living or dead organisms can be examined or manipulated. The following parts are advantageous as components for use of this system or kit for magnetic attraction of therapeutic cells via an endoscope:
  i. a guide element comprising a spring elastic distal area and a proximal area,
  ii. one or more magnetic elements having detection molecules which are used between the distal area and the proximal area of the guide elements,
  iii. a stabilizing element connected to the proximal area of the guide element,
  iv. an adapter and
  v. a longitudinally movable sleeve.

The length of the entire instrument comprising the guide element, the magnetic element and the stabilizing element should be selected, so that after endoscope placement, usually via the instrument channel of the endoscope, the endoscope can be removed from the body without altering the position of the instrument. This can be accomplished by the fact that the total length of the instrument is adapted to the total length of the endoscope. It will be readily possible for a knowledgeable person skilled in the art to construct possible special forms of the instrument in which the magnetic element comprises two or more magnetic component elements with different detection molecules and being arranged between the distal and proximal portions of the guide element or performing the functionalization of the distal portion of the guide element using detection molecules while preserving the spring elastic material properties of this region.

The use for magnetic attraction of therapeutic cells is advantageous, where the magnetic instrument is introduced into a vascular system through a vascular access. In this way the instrument can be placed quickly and easily at a site of action and magnetically labeled therapeutic cells can be conveyed to that site through magnetic attraction. Furthermore, this permits a rapid and in particular an efficient extraction of excess cells from the site of action. The following additional components are appropriate for use of the instrument or the kit through a vascular access:
  i. a blood vessel indwelling cannula with a puncture needle;
  ii. an adapter which can be attached to the blood vessel indwelling cannula and by means of which the instrument can be positioned intravascularly;
  iii. a port which is designed preferably on the adaptor and by means of which an infusion solution can be administered during the dwell time of the instrument in the patient's body and/or
  iv. a transparent or displaceable sleeve which can be pushed onto the adapter, surrounding the instrument outside of the body and ensuring hygienic handling during its dwell time in the body.

Due to the advantageous embodiment, homing of magnetically labeled therapeutic cells or extraction of these cells from the body with a high yield can be achieved easily and efficiently when the instrument is inserted into a vascular system through a vascular access. This embodiment thus constitutes a substantial facilitation of work for hospital personnel.

Furthermore, the system or the kit can be used for magnetic attraction of therapeutic cells for interventional treatment of disease selected from the group comprising congenital diseases, proliferative diseases, inflammatory diseases, autoimmune diseases, infectious diseases, hormonal diseases, diseases of the blood and the hematopoietic organs, diseases of the digestive tract, the liver, the gallbladder, the pituitary, diseases of the urogenital tract and the kidneys, diseases of the heart, pathological changes in the blood vessel system and the lymphatic system, diseases of the lungs, diseases of the central or peripheral nervous system as well as the electric stimulus conduction system and neurodegenerative diseases. The instrument here and/or the kit may be used to convey magnetically labeled therapeutic cells to the site of action of the corresponding disease, such that excess cells present at the site of action can removed easily and quickly by the instrument. The system or the kit can surprisingly be used for diagnosis or for achieving an intermediate step along the way to making a diagnosis and/or for controlling the course of treatment of the following diseases:
  Congenital diseases, preferably comprising autosomally recessive, autosomally dominant, gonosomal and mitochondrial and/or extrachromosomal congenital diseases and/or a disease that can be attributed to a genetic predisposition.
  Proliferative diseases preferably comprising tumors, precancerous conditions, dysplasia, neuroendocrine tumors, endometriosis and/or metaplasia.
  Autoimmune diseases preferably comprising rheumatoid arthritis, inflammatory intestinal disease, neuropathic pain, alopecia areata, psoriasis, psoriatic arthritis, acute pancreatitis, allograft rejection, allergies, allergic inflammation of the lungs, multiple sclerosis, Alzheimer's disease, Crohn's disease and/or systemic lupus erythematosus.

Infectious diseases preferably comprising infections caused by parasitic diseases, bacterial diseases and/or viral diseases.

Hormonal diseases preferably comprising diseases of the sugar metabolism, the fat metabolism, the protein metabolism, sexual development and reproduction, the water-salt balance, growth and/or cell formation.

The surprising use of the system or kit for magnetic attraction of magnetically labeled therapeutic cells for treatment of the aforementioned diseases constitutes a departure from what is customary in the art because it is not disclosed in the state of the art that diseases can be treated successfully with the help of a magnetic instrument and homing.

The invention also relates to a method for magnetic attraction of therapeutic cells, comprising the following steps:
 a. Selection of therapeutic cells,
 b. Labeling the cells with magnetic particles,
 c. Introducing the cells according to b into a body
 d. Introducing an instrument into the body such that the instrument has a magnetic element and
 e. Magnetic attraction and binding of the labeled cells by the magnetic element of the instrument.

For this method, the preferred embodiments of the system already mentioned above are applicable accordingly. Those skilled in the art will know how they must select therapeutic cells because this depends on the disease to be treated. The cells can be labeled magnetically with the labeling method described above (e.g., transfection). The magnetically labeled cells, in particular a therapeutic cell may be administered through a vascular access, in which case it is also possible to introduce the cells into a body or an organism through a puncture. The instrument (a medical product which can be identified as a therapeutic aid) is introduced through a puncture cannula or is introduced endoscopically into a vein or an artery or some other cavity in the body (e.g., abdominal cavity, chest, bile duct, efferent urinary tract, gastrointestinal tract) or via a needle biopsy device into the interior of a solid organ.

In a preferred embodiment the invention relates to a method for magnetic attraction of therapeutic cells comprising the following steps:
 a. Selection of therapeutic cells,
 b. Labeling of cells with magnetic particles,
 c. Introducing the cells according to b into a body,
 d. Introducing an instrument into the body such that the instrument has a magnetic element and/or
 e. Magnetic attraction and binding of the labeled cells by the magnetic element of the instrument.

The steps of this method can be combined with one another in different combinations and adapted to requirements.

Furthermore, the invention relates to a device comprising the following components:
 i. a guide element comprising a spring elastic distal area and a proximal area,
 ii. a magnetic function element which is introduced between the distal area and the proximal area of the guide element, and
 iii. a stabilizing element connected to the proximal area of the guide element.

This device is used for magnetic attraction of magnetically labeled therapeutic cells. In particular the device is used for homing of magnetically labeled therapeutic cells. In addition the device is used for extraction or minimally invasive elimination of magnetically labeled therapeutic cells from a body or organism. The statements made about the system, the kit and the use of the system or kit also apply to the device accordingly. Those skilled in the art are aware of how they can transfer the disclosed technical teaching for the system to the device.

Advantages of the instrument according to the invention include: cost reduction, simplification, savings of time, materials, work steps, costs or scarce and difficult to acquire raw materials, increased reliability, elimination of errors, improving quality, freedom from maintenance, greater efficacy, higher yield, increasing technical options, opening up a new field, first solution to a problem, possibility of economizing or miniaturization.

The present invention will now be described on the basis of figures as an example, but only the embodiment of the invention based on three elements will be performed here. A specialist can readily select other compositions of these elements or make a reduction in the number of components based on this description in order to achieve the desired function.

Figure 2:
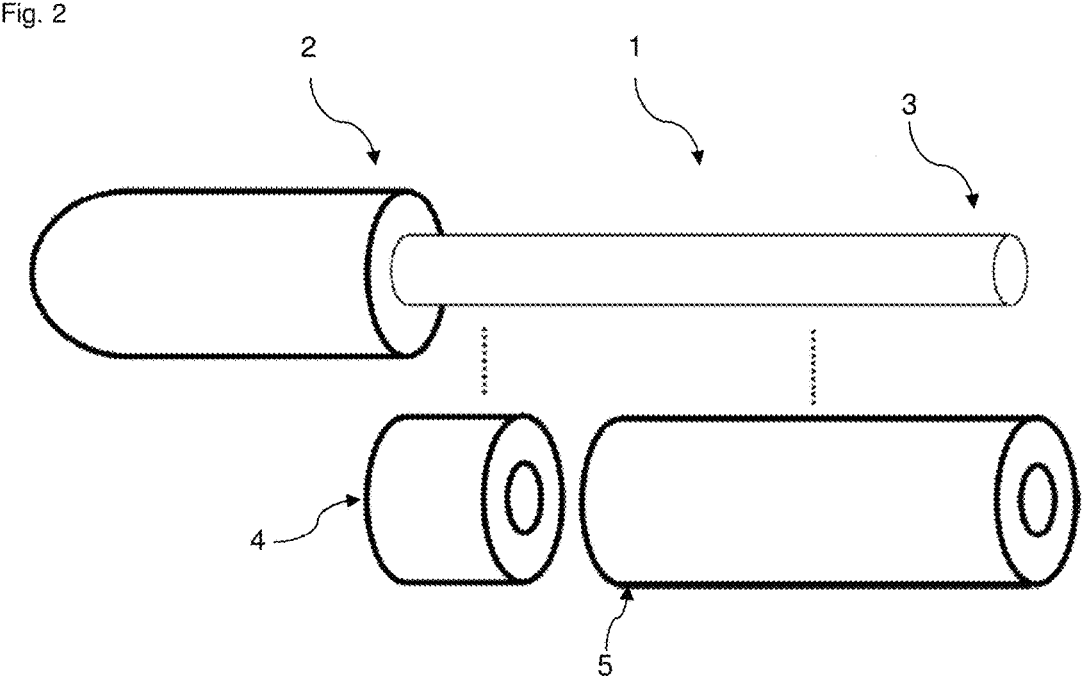
Figure 3:
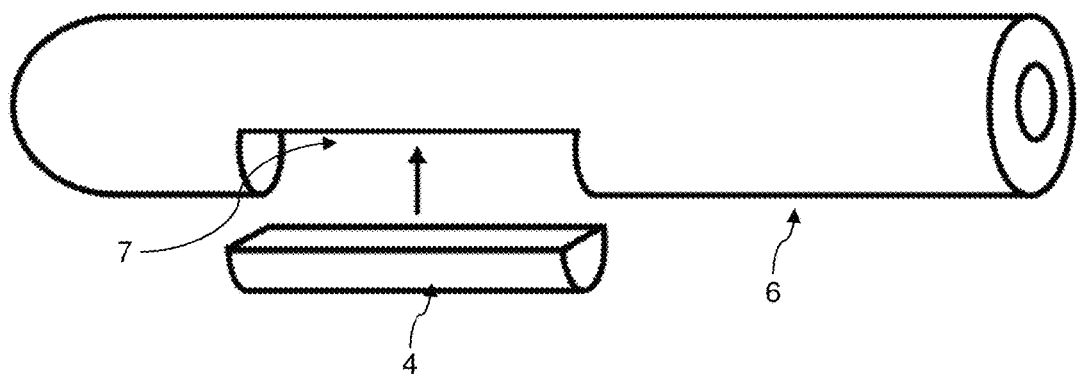
Figure 4:
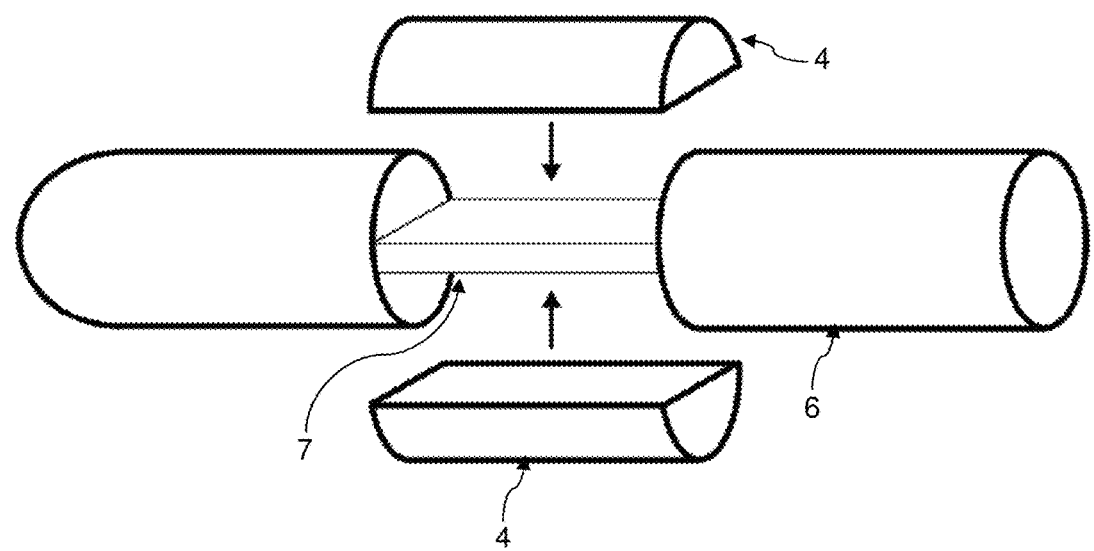
Figure 5:
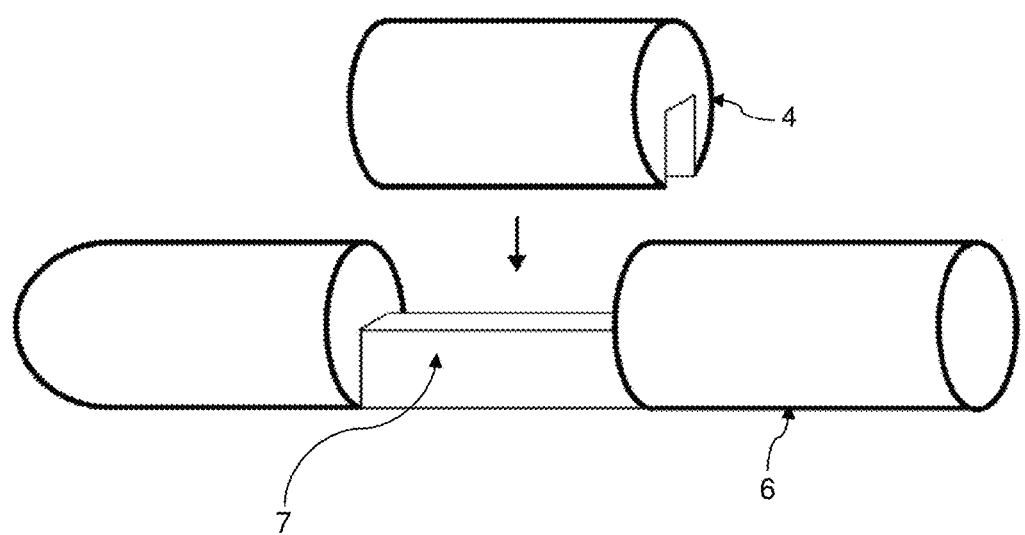
Figure 6:
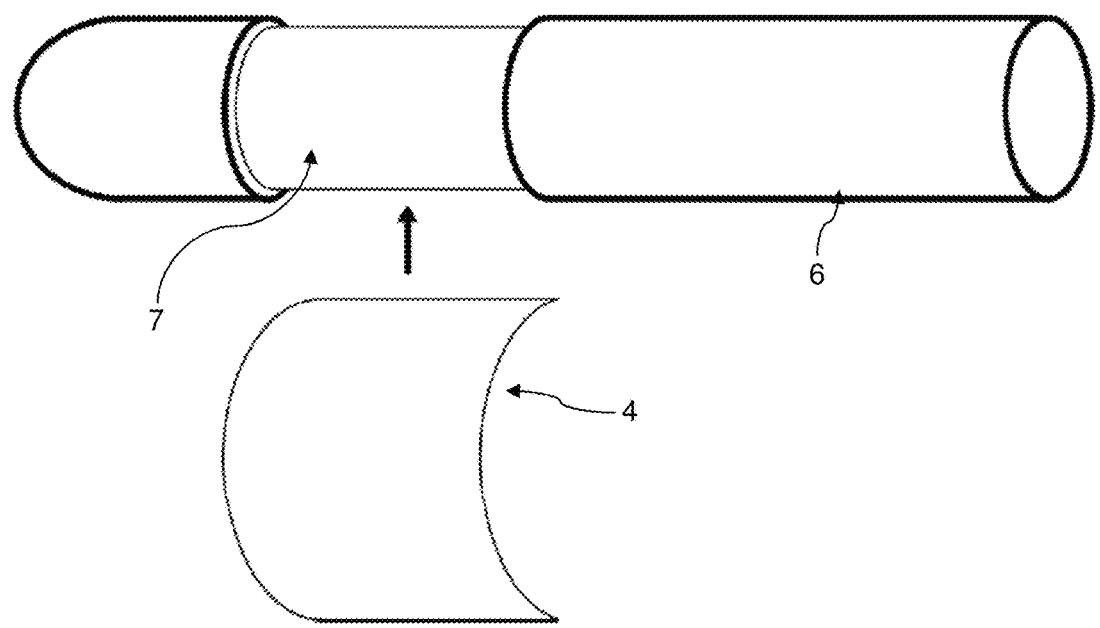
Figure 7:
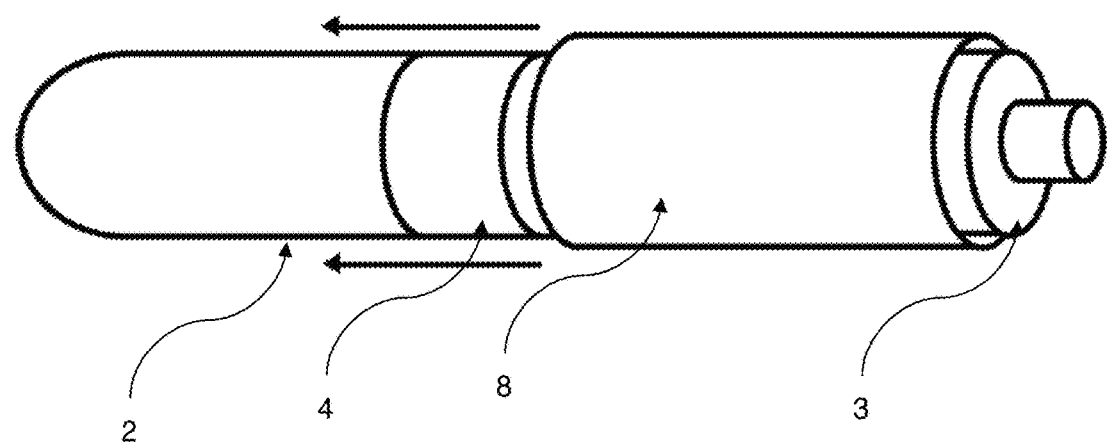
Figure 8:
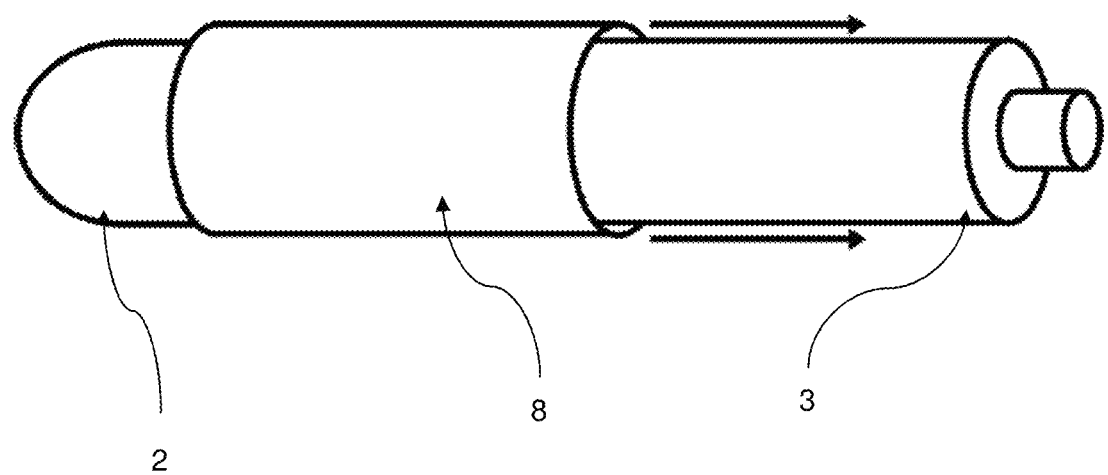

FIG. 1 shows a side view of a guide element with a distal area and a proximal area, FIG. 2 shows a side view of a guide element with a cylindrical magnetic element and a cylindrical stabilizing element, FIG. 3 shows a side view of an instrument for homing of therapeutic cells with a receiving device for one semicylindrically shaped magnetic element, FIG. 4 shows a side view of an instrument for homing of therapeutic cells with a receiving device for two semicylindrically shaped magnetic elements, FIG. 5 shows a side view of an instrument for homing of therapeutic cells with a web-shaped receiving device for a magnetic element shaped like a clasp, FIG. 6 shows a side view of an instrument for homing of therapeutic cells with a receiving device for a magnetic element shaped like a film, FIG. 7 shows a side view of an instrument for homing of therapeutic cells with a cover device and FIG. 8 shows a side view of an instrument for homing of therapeutic cells with a cover device over a magnetic element.

Figure 9:
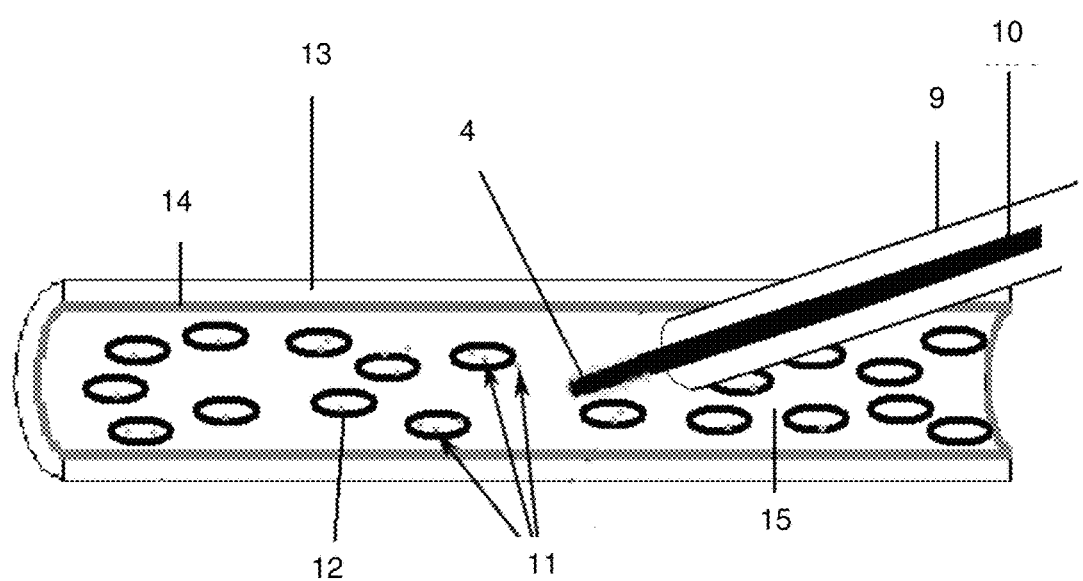

FIG. 9 shows the use of a preferred system.

FIG. 1 shows a schematic side view of a guide element. The guide element 1 consists of a distal area 2 and a proximal area 3. The distal area 2 of the guide element 1 has a spring elastic design. It may be made of metals, preferably steel. Alternatively, however, nonmetallic materials of which thin cylindrically structures can be shaped may be used for this component. Polymer materials, e.g., polytetrafluoroethylene may be used for this purpose. The distal area 2 of the guide element 1 is fixedly connected to the proximal area 3. However, the distal area 2 and the proximal area 3 of the guide element 1 may also be produced in a manufacturing process if this material allows, which is possible when using suitable plastics in the production, for example.

FIG. 2 shows a schematic side view of a guide element with a magnetic element and a stabilizing element. The magnetic element 4 in FIG. 2 may additionally have binding molecules on its surface which react with specific cells and/or molecules in the body of humans and animals and thereby permit an improved enrichment of specimen material in situ. This element is essentially to be designed as a cylindrical hollow body which is of such dimensions that it can be applied to the guide element 1 from the proximal area 3. To do so the inside diameter of this component is larger than the outside diameter of the proximal area 3 of the guide element 1. The outside diameter of the magnetic element 4 in relation to the distal are of the guide element 1 may be larger or smaller or the same. The outside diameter of the magnetic element 4 is preferably 0.01 to 0.1 mm smaller than the outside diameter of the distal area 2 of the guide element 1. Materials for producing these components include metals, plastics or ceramic materials which may serve as the substrate for anchoring detection molecules. A design in the form of tiny hollow fibers or sponges is also possible.

In addition, FIG. 2 shows a stabilizing element 5. This component is characterized in that it is tubular and can be applied with an accurate fit to the proximal area 3 of the guide element 1. The outside diameter of the stabilizing element 5 corresponds to the outside diameter of the distal portion 2 of the guide element 1. The wall thickness of this tubular element is of such dimensions that the magnetic element 4 is secured on the guide element 1 by the stabilizing element 5 in a slip-proof manner. The stabilizing element 5 and the proximal area 3 of the guide element 1 can therefore enter into a stable connection, which can be implemented, for example, by gluing or welding these elements onto the proximal end of the instrument without any loss of function. In addition it is advantageous if the two components are reversibly joined to one another. By using materials for the stabilizing element which impart rubber elastic properties to it, instruments for homing of therapeutic cells can be produced such that these instruments can be positioned optimally at different locations in the body.

FIG. 3 shows a side view of an instrument for homing of therapeutic cells with a receiving device for a semicylindrically shaped magnetic element. The guide element 1 and the stabilizing element 5 may be manufactured in a manufacturing process and permanently joined together accordingly. The guide element/stabilizing element 6 manufactured in this way has a receiving device 7, which serves to receive a magnetic element 4. The shape of the receiving device 7 may have different forms such as the shape of a semicylinder. The magnetic element 4 is shaped according to the receiving device 7. This permits a variation in specimens to be collected or permits rapid and easy replacement of the magnetic element 4 to adapt this to new situations.

FIG. 4 shows a side view of an instrument for homing of therapeutic cells with a receiving device for two semicylindrically shaped magnetic elements. This instrument may be designed so half the guide element 1 and the stabilizing element 5 from FIG. 2 are manufactured in one manufacturing method, yielding a guide element/stabilizing element 6 and having a receiving device 7 into which two magnetic elements 4 can be introduced. The receiving device 7 may be designed so that two semicylindrically shaped magnetic elements 4 can be inserted into it. Different detection molecules may be applied to the two magnetic elements 4, consequently allowing and/or improving the enrichment of different cells and/or molecules. In addition, the yield of specimen can be increased by such a design.

FIG. 5 shows a side view of an instrument for homing of therapeutic cells with a web-shaped receiving device for a clasp-shaped magnetic element. The receiving device 7 may be designed so that it has a web shape and can receive a clasp-shaped magnetic element 4 accordingly. The magnetic element 4 designed in this way can be replaced rapidly. In this alternative embodiment, a magnetic element 4 is also arranged between a distal area 2 and a proximal stabilizing element 5. This achieves the result that with a minimal risk of injury to the patient, the biofunction of the instrument is ensured and the instrument can be removed from the body as a whole after the homing process of the therapeutic cells in situ.

FIG. 6 shows a side view of an instrument for homing of therapeutic cells with a receiving device for a film-shaped magnetic element. In applications which demand a reduction in the outside diameter of the instrument, a film-shaped receiving device 7 may serve to receive a film-shaped magnetic element 4. A film-shaped magnetic element in the sense of the present invention denotes a shape having a very small thickness and a large area. This embodiment can be used in particular in small vessels in which therapeutic cells must be deposited. Special detection molecules in the form of an inorganic material with which the enrichment of certain organic and/or inorganic molecules can be achieved can thus be introduced into the receiving device 7. Therefore the receiving device for homing of therapeutic cells may also be used for enrichment of cells and/or molecules which are present in low concentrations in regions of the body.

FIG. 7 shows a side view of an instrument for homing of therapeutic cells having a cover device. A cover device 8 which may comprise a sleeve-shaped structure on which the instrument slides is shown here. This cover device 8 is applied to the instrument from the proximal area of the guide elements. Suitable materials for the cover device 8 include polymers, preferably polytetrafluoroethylene. In particular when the adjacent components are made of the same material, a good displaceability of the individual components is achieved in this way.

FIG. 8 shows a side view of an instrument for homing of therapeutic cells with a cover device over a magnetic element. The cover device 8 here is applied to the guide element/stabilizing element 6 and serves to cover the magnetic element 4 on which the therapeutic cells are located. After reaching the location for cell deposition, the cover device is removed from the magnetic element 4 in the proximal direction so that the magnetic element 4 and the therapeutic cells are released for deposition.

FIG. 9 shows an application of a preferred system. A cannula 9 is inserted into a blood vessel, e.g., a vein 13 preferably through a vascular access. The vein is covered with an endothelium 14 through which blood 15 flows. Furthermore, magnetic particles 11 and cells 12 that are magnetically labeled with these particles are present in the vein 13. The magnetic particles 11 as well as the magnetically labeled cells 12 are conveyed to a site of action with the help of the magnetic function element 4 of the instrument (=homing). Furthermore, it is possible through the use of this instrument to remove excess magnetically labeled cells 12 and magnetic particles 11 from the vein 13. To improve the homing of therapeutic cells 12 in damaged tissue areas of a patient, the magnetic particles 11 which are either already been used for cell separation or cell labeling or are comparable are also used to bind the cells by magnetic forces to a suitably designed magnetic instrument 4. With the help of the magnetic instrument 4, therapeutic cells 12 can be introduced interventionally into damaged tissue areas locally (homing) through the blood vessel system or through tissue puncture. Furthermore, excess cells 12 can be eliminated from the body by magnetic forces so that the risk potential of therapeutic cells can be drastically reduced. It has surprisingly been found that the use of magnetic function elements 4 within an instrument results in a substantial improvement in the number of therapeutic cells 12 in the damaged tissue areas, namely from max. 20% at the present time to 60% deposition success.

LIST OF REFERENCE NUMERALS

1 Guide element
2 Distal area
3 Proximal area
4 Magnetic element
5 Stabilizing element
6 Guide element/stabilizing element
7 Receiving device
8 Cover device
9 Cannula
10 Wire
11 Magnetic particle
12 Magnetic cell
13 Vein
14 Endothelium
15 Blood

The invention claimed is:

1. A method for magnetic attraction of therapeutic cells comprising:
   a. selecting therapeutic cells.
   b. labeling of the cells with magnetic particles to produce therapeutic labeled cells,
   c. introducing the therapeutic labeled cells according to b. into a body,
   d. introducing a device into the body wherein the device comprises:
      i. a guide element comprising a spring elastic distal area and a proximal area,
      ii. a magnetic function element which is introduced between the distal area and the proximal area of the guide element, and
      iii. a stabilizing element which is connected to the proximal area of the guide element and
   e. magnetically attracting and binding of the labeled therapeutic cells by the magnetic element of the device.

2. The method according to claim 1, wherein the therapeutic cells are magnetically attracted in a blood vessel system, efferent glandular ducts of the pancreatic gland, lacrimal gland, parotid gland, efferent glandular ducts of the mucous glands, mixed glands, skin and appendage glands, mammary glands, spinal canal, cerebral ventricle system, peridural space, gallbladder and its efferent anatomical structures, efferent urinary tract or a lymphatic system, body cavities of an abdomen, chest, uterus, urogenital apparatus or a joint or gastrointestinal tract.

3. The method of claim 1, wherein said method is configured for endoscopic administration, wherein the device further comprises:
   iv. an adapter and
   v. a longitudinally movable sleeve, wherein the magnetic function element comprises one or more magnetic elements having detection molecules, and
   endoscopically administering the therapeutic cells and magnetically attracting them via said one or more magnetic elements.

4. The method of claim 1, wherein the device is introduced into a vascular system via a vascular access.

5. The method of claim 1, wherein the therapeutic cells are magnetically attracted in course of a interventional treatment of disease selected from the group consisting of congenital diseases, proliferative diseases, inflammatory diseases, autoimmune diseases, infectious diseases, hormonal diseases, diseases of blood and hematopoietic organs, diseases of the digestive tract, liver, the gallbladder, pancreatic gland, diseases of the urogenital tract and the kidneys, diseases of the heart, pathological changes in the blood vessel system and the lymphatic system, diseases of lungs, diseases of the central or peripheral nervous system and neurodegenerative diseases.

6. The method of claim 5, wherein the congenital diseases are selected from the group consisting of an autosomally recessive disease, an autosomally dominant disease, a gonosomal and mitochondrial and/or extrachromosomal disease or a disease that can be attributed to a genetic predisposition.

7. The method of claim 5, wherein the proliferative diseases are selected from the group consisting of a tumor, a precancerous condition, a dysplasia, a neuroendocrine tumor, an endometriosis and a metaplasia.

8. The method of claim 5, wherein the autoimmune diseases are selected from the group consisting of rheumatoid arthritis, inflammatory intestinal disease, osteoarthritis, neuropathic pain, alopecia areata, psoriasis, psoriatic arthritis, acute pancreatitis, allograft rejection, allergies, allergic inflammations of the lungs, multiple sclerosis, Alzheimer's disease, Crohn's disease and systemic lupus erythematosus.

9. The method of claim 5, wherein the infectious diseases are selected from the group consisting of a parasitic disease, a bacterial disease and a viral disease.

10. The method of claim 5, wherein the hormonal diseases are selected from the group consisting of a disease relating to sugar metabolism, fat metabolism, protein metabolism, sexual development and reproduction, water-salt balance, growth and cell production.

* * * * *